US012751700B2

(12) United States Patent

Konno

(10) Patent No.: US 12,751,700 B2
(45) Date of Patent: Oct. 6, 2026

(54) MAMMOGRAPHY APPARATUS, CONTROL DEVICE, AND PROGRAM

(71) Applicant: FUJIFILM CORPORATION, Tokyo (JP)

(72) Inventor: Shinichiro Konno, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 216 days.

(21) Appl. No.: 18/808,025

(22) Filed: Aug. 18, 2024

(65) Prior Publication Data

US 2025/0064434 A1 Feb. 27, 2025

(30) Foreign Application Priority Data

Aug. 21, 2023 (JP) ................................ 2023-134029

(51) Int. Cl.
*A61B 10/02* (2006.01)
*A61B 90/00* (2016.01)

(52) U.S. Cl.
CPC .......... *A61B 10/0233* (2013.01); *A61B 90/37* (2016.02); *A61B 2010/0208* (2013.01); *A61B 2090/376* (2016.02)

(58) Field of Classification Search
CPC ................ A61B 10/0233; A61B 90/37; A61B 2010/0208; A61B 2090/376
See application file for complete search history.

(56) References Cited

U.S. PATENT DOCUMENTS

2010/0249647 A1* 9/2010 Nakayama ............. A61B 90/17 600/567
2022/0096024 A1 3/2022 Fujimoto et al.
2022/0096042 A1 3/2022 Gemma

FOREIGN PATENT DOCUMENTS

JP 2010-194194 A 9/2010
JP 2022-057948 A 4/2022
JP 2022-057951 A 4/2022

* cited by examiner

*Primary Examiner* — Kiho Kim
(74) *Attorney, Agent, or Firm* — Studebaker Brackett PLLC

(57) ABSTRACT

A control device of a mammography apparatus is provided. The mammography apparatus includes a biopsy device, an imaging table, and an arm in which a radiation irradiator and a projector are provided on one end portion side and a relative angle between the radiation irradiator and an imaging surface of the imaging table is changeable. The radiation irradiator emits radiation for imaging of a radiation image toward the imaging surface of the imaging table. The control device includes at least one processor that is configured to control the arm such that the relative angle is a predetermined tilt angle in a case where biopsy using a longitudinal puncture is performed by the biopsy device.

15 Claims, 10 Drawing Sheets

FIG. 7

DISTORTION CORRECTION INFORMATION DATABASE

| TILT ANGLE (DEGREE) | COORDINATE CONVERSION TABLE |
|---|---|
| −20 | (COORDINATE CONVERSION TABLE 1) |
| −18 | (COORDINATE CONVERSION TABLE 2) |
| ⋮ | ⋮ |
| +18 | (COORDINATE CONVERSION TABLE 19) |
| +20 | (COORDINATE CONVERSION TABLE 20) |

FIG. 8

TILT ANGLE DATABASE

| IMAGING CONDITION | TILT ANGLE (DEGREE) |
|---|---|
| STEREO IMAGING | ±15 |
| TOMOSYNTHESIS IMAGING | ±20 |

MAMMOGRAPHY APPARATUS, CONTROL DEVICE, AND PROGRAM

CROSS-REFERENCE TO RELATED APPLICATION

This application claims priority from Japanese Patent Application No. 2023-134029, filed Aug. 21, 2023, the disclosure of which is incorporated herein by reference in its entirety.

BACKGROUND

Technical Field

The present disclosure relates to a control device of a mammography apparatus, a system including a mammography apparatus, and a non-transitory storage medium storing a program.

Related Art

In the related art, a technology of providing a projector in a mammography apparatus and projecting various information is known (refer to, for example, JP2022-057948A and JP2022-057951A).

In this technology, in consideration of projecting information onto an upper surface of a compression plate, an imaging surface of an imaging table, an upper side of a breast, or the like in the mammography apparatus, an information projection port of the projector is preferably provided near a radiation emission port of a radiation irradiator provided at an upper portion of an arm in the mammography apparatus. For example, in a case where necessary information is projected onto the upper surface of the compression plate, a radiologist can perform positioning of a breast of a subject while checking the information without moving the line of sight by a large amount.

In addition, in a mammography apparatus provided with a biopsy device, a technology of projecting necessary information such as a puncture position and target information is also disclosed (refer to, for example, JP2010-194194A).

However, in the technology disclosed in JP2010-194194A, in a case of performing a longitudinal puncture, parts, such as a biopsy needle unit of a biopsy device that includes a biopsy needle and a holder or the like which holds the biopsy needle, a moving mechanism that moves the biopsy needle unit, and the like, are disposed immediately above the breast. For this reason, depending on positions of the parts, a projection image from the projector may be shielded, and in this case, there is a problem that visibility of the projection image is deteriorated.

SUMMARY

The present disclosure has been made in view of the above circumstances, and an object of the present disclosure is to provide a control device of a mammography apparatus, a system including a mammography apparatus, and a non-transitory storage medium storing a program capable of improving visibility of a projection image as compared with the related art.

In order to achieve the above object, according to a first aspect of the present disclosure, there is provided a mammography apparatus including a biopsy device, an imaging table, and an arm in which a radiation irradiator and a projector are provided on one end portion side and a relative angle between the radiation irradiator and an imaging surface of the imaging table is changeable, the radiation irradiator emitting radiation for imaging of a radiation image toward the imaging surface of the imaging table, the mammography apparatus comprising: at least one processor, in which the processor is configured to control the arm such that the relative angle is a predetermined tilt angle in a case where biopsy using a longitudinal puncture is performed by the biopsy device.

According to a second aspect of the present disclosure, in the mammography apparatus according to the first aspect, in a case of performing tilt imaging other than imaging in which the imaging table, the radiation irradiator, and the biopsy device are arranged in a straight line, the predetermined tilt angle is an angle according to the tilt imaging.

According to a third aspect of the present disclosure, in the mammography apparatus according to the second aspect, the tilt imaging is imaging of at least one of stereo imaging or tomosynthesis imaging.

According to a fourth aspect of the present disclosure, in the mammography apparatus according to any one of the first aspect to the third aspect, the processor is configured to control the arm such that the relative angle is the predetermined tilt angle and the arm is tilted toward a side away from a position of an operator who performs imaging of the radiation image.

According to a fifth aspect of the present disclosure, in the mammography apparatus according to any one of the first aspect to the third aspect, the processor is configured to control the arm such that the relative angle is the predetermined tilt angle and the arm is tilted toward a side opposite to a right-left direction of a breast for which the biopsy is to be performed.

According to a sixth aspect of the present disclosure, in the mammography apparatus according to any one of the first aspect to the third aspect, the processor is configured to: control the arm such that the relative angle is the predetermined tilt angle and the arm is tilted toward a side away from a position of an operator who performs imaging of the radiation image; control the arm such that the relative angle is the predetermined tilt angle and the arm is tilted toward a side opposite to a right-left direction of a breast for which the biopsy is to be performed, and in a case in which the side away from the position of the operator and the side opposite to the right-left direction of the breast are different from each other, control the arm such that the arm is tilted toward the side away from the position of the operator.

According to a seventh aspect of the present disclosure, in the mammography apparatus according to the first aspect, the processor is configured to adjust the relative angle according to a drive position of the biopsy device.

According to an eighth aspect of the present disclosure, in the mammography apparatus according to the first aspect, the processor is configured to adjust a projection position of a projection image by the projector according to a drive position of the biopsy device.

According to a ninth aspect of the present disclosure, in the mammography apparatus according to the first aspect, the processor is configured to adjust the relative angle according to a position of a compression plate provided on the imaging surface side of the imaging table.

According to a tenth aspect of the present disclosure, in the mammography apparatus according to the first aspect, the processor is configured to correct a distortion of a projection image that is caused by the projector and occurs in a case where the relative angle is set to the tilt angle.

According to an eleventh aspect of the present disclosure, in the mammography apparatus according to the first aspect, the processor is configured to control the arm such that the relative angle is a preset tilt angle regardless of an imaging condition in a case where biopsy using a longitudinal puncture is performed by the biopsy device.

Further, in order to achieve the above object, according to a twelfth aspect of the present disclosure, there is provided a control device that controls a mammography apparatus, the mammography apparatus including a biopsy device, an imaging table, and an arm in which a radiation irradiator and a projector are provided on one end portion side and a relative angle between the radiation irradiator and an imaging surface of the imaging table is changeable, the radiation irradiator emitting radiation for imaging of a radiation image toward the imaging surface of the imaging table, the control device comprising: at least one processor, in which the processor is configured to control the arm such that the relative angle is a predetermined angle in a case where the biopsy device interferes with a projection region by the projector, the predetermined angle being an angle at which a light shielding region by the biopsy device that is included in a projection image by the projector has an area equal to or smaller than a predetermined area.

Further, in order to achieve the above object, according to a thirteenth aspect of the present disclosure, there is provided a non-transitory storage medium storing a program causing a computer to perform control processing of a mammography apparatus, the mammography apparatus including a biopsy device, an imaging table, and an arm in which a radiation irradiator and a projector are provided on one end portion side and a relative angle between the radiation irradiator and an imaging surface of the imaging table is changeable, the radiation irradiator emitting radiation for imaging of a radiation image toward the imaging surface of the imaging table, the control processing comprising: controlling the arm such that the relative angle is a predetermined tilt angle in a case where biopsy using a longitudinal puncture is performed by the biopsy device.

Further, in order to achieve the above object, according to a fourteenth aspect of the present disclosure, there is provided a non-transitory storage medium storing a program causing a computer to perform control processing of a mammography apparatus, the mammography apparatus including a biopsy device, an imaging table, and an arm in which a radiation irradiator and a projector are provided on one end portion side and a relative angle between the radiation irradiator and an imaging surface of the imaging table is changeable, the radiation irradiator emitting radiation for imaging of a radiation image toward the imaging surface of the imaging table, the control processing comprising: controlling the arm such that the relative angle is a predetermined angle in a case where the biopsy device interferes with a projection region by the projector, the predetermined angle being an angle at which a light shielding region by the biopsy device that is included in a projection image by the projector has an area equal to or smaller than a predetermined area.

According to the present disclosure, the visibility of the projection image can be improved as compared with the related art.

BRIEF DESCRIPTION OF THE DRAWINGS

FIG. 7 is a schematic diagram illustrating an example of a configuration of a distortion correction information database according to the embodiment.

FIG. 8 is a schematic diagram illustrating an example of a configuration of a tilt angle database according to the embodiment.

DETAILED DESCRIPTION

Figure 1:
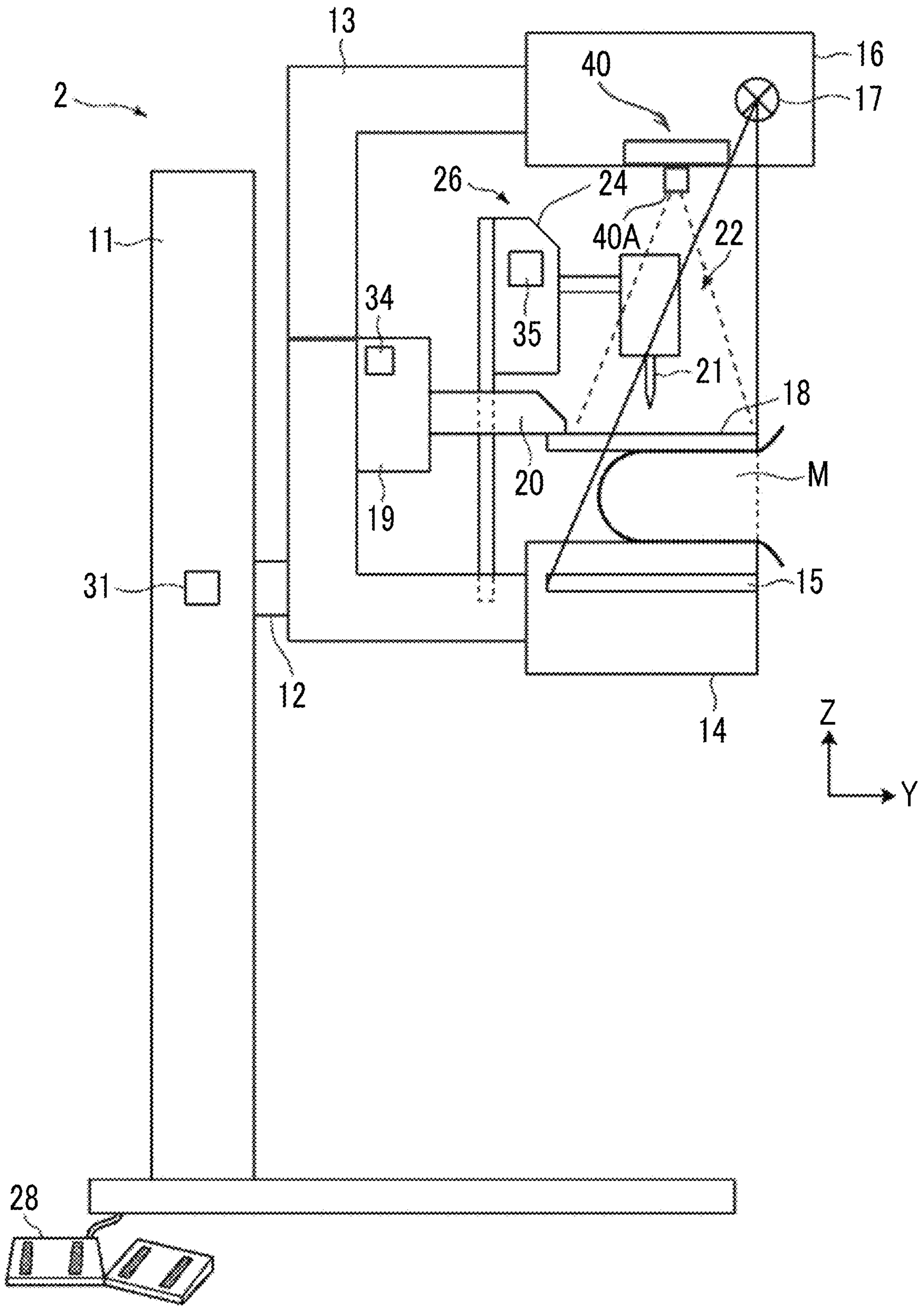
FIG. 1 is a schematic configuration diagram illustrating an example of a mammography apparatus according to an embodiment.

Hereinafter, an example of an embodiment for implementing the technology of the present disclosure will be described in detail with reference to the drawings. First, a mammography apparatus 2 according to the present embodiment will be described in detail with reference to FIG. 1 to FIG. 4. FIG. 1 is a schematic configuration diagram illustrating an example of the mammography apparatus 2 according to the present embodiment.

As an example, as illustrated in FIG. 1, in the mammography apparatus 2 according to the present embodiment, a radiation housing unit 16 in which a radiation irradiator 17 is housed inside and an imaging table 14 are connected to an arm 13 to face each other. An image recording medium such as a radiation detector 15 is set inside the imaging table 14 in a state of being housed in a recording medium holding portion such as a cassette. The arm 13 is attached to a base 11 with a C axis 12. In addition, the arm 13 is provided to the base 11 by attaching the C axis 12, which is the center of rotation, to a center position of the radiation detector 15 such that the center of rotation of the arm 13 is the center of the radiation detector 15 in an X direction (refer to FIG. 2).

The base 11 is provided with an operation unit 28 that receives a radiation irradiation instruction from the radiation irradiator 17 and is used to allow an operator (hereinafter, also referred to as an "operator") to adjust a height of the imaging table 14 (that is, a height of the arm 13) and a tilt of the imaging table 14 (that is, a tilt of the arm 13), and an arm controller 31 that vertically moves the arm 13 and rotates the arm 13 in accordance with an input from the operation unit 28.

The arm controller 31 adjusts the tilt of the arm 13 by rotating the C axis 12 attached to the base 11, and adjusts the height of the imaging table 14 by vertically moving the arm 13.

At a central portion of the arm 13, a compression plate 18 that is disposed above the imaging table 14 to hold and compress the breast, a support portion 20 that supports the compression plate 18, and a moving mechanism 19 that moves the support portion 20 in a vertical direction along the arm 13. The position and compression pressure of the compression plate 18 are controlled by a compression plate controller 34.

Figure 2:
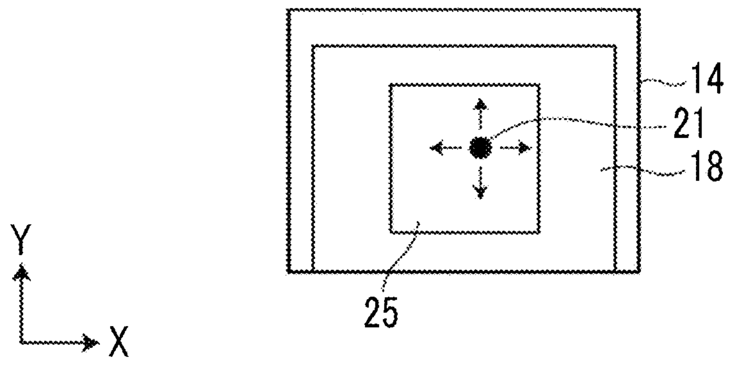
FIG. 2 is a schematic plan view of a compression plate in the mammography apparatus according to the embodiment, viewed from above.

FIG. 2 is a view of the compression plate 18 viewed from above. As illustrated in FIG. 2, the compression plate 18 is provided with an opening portion 25 of approximately 10×10 cm square such that a biopsy can be performed on the breast fixed by the imaging table 14 and the compression plate 18.

As an example, a biopsy unit 26 as a biopsy device of the present disclosure illustrated in FIG. 1 comprises a biopsy needle 21 that is inserted into a breast and a biopsy needle unit 22, and further comprises a moving mechanism 24 that moves the biopsy needle unit 22 in X, Y, and Z directions. The position of a distal end of the biopsy needle 21 of the biopsy needle unit 22 is controlled by a needle position controller 35 of the moving mechanism 24. Note that, in FIG. 2, a horizontal direction is the X direction, a vertical direction is the Y direction, and a direction perpendicular to an XY plane is the Z direction.

On the other hand, a projector 40 in which a projection unit 40A is provided on a lower surface of the radiation housing unit 16 and near an emission port of the radiation emitted by the radiation irradiator 17 is built in the radiation housing unit 16. The projector 40 is mainly configured to project an image (hereinafter, referred to as a "projection image") indicating various information to an upper surface of the compression plate 18. On the other hand, in a case where the compression plate 18 is detached, the projector 40 can project a projection image on an upper surface (hereinafter, also referred to as an "imaging surface") of the imaging table 14 or the breast in a state where the breast is not compressed by the compression plate 18. As the projector 40, known projectors, such as a liquid crystal projector, a digital light processing (DLP) (registered trademark) projector, and a laser projector, can be applied.

As described above, the mammography apparatus 2 according to the present embodiment is provided with the biopsy unit 26 and the arm 13. On one end portion side of the arm 13, the radiation irradiator 17 that emits radiation for imaging of a radiation image toward the imaging surface of the imaging table 14 and the projector 40 are provided. On the other end side of the arm 13, the imaging table 14 is provided.

Figure 3:
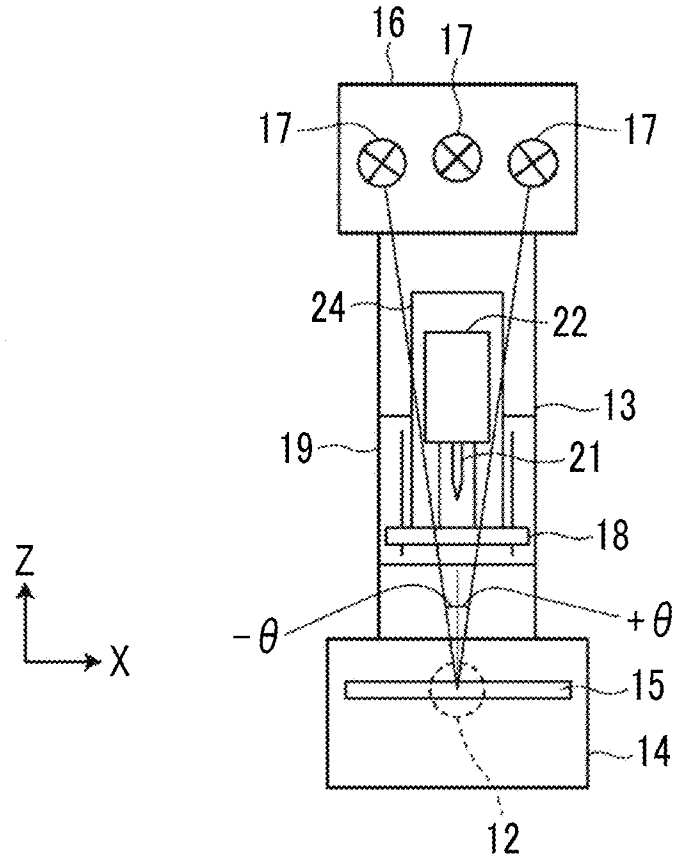
FIG. 3 is a diagram illustrating an example of a state in a case where a radiation irradiator in the mammography apparatus according to the embodiment is tilted in a right-left direction from a direction along an arm.

Note that the mammography apparatus 2 acquires scout images which include a target region of the breast to be biopsied and are imaged from two directions before a puncture is performed. The scout image is an image viewed from different viewpoints in order to check the position to be pathologically examined. For example, as illustrated in FIG. 3, two partial images obtained by performing imaging from directions in which the radiation irradiator 17 is tilted in a right-left direction (for example, tilted by 15° in the directions of +θ and −θ illustrated in FIG. 3) from a direction along the arm 13 are set as the scout images.

Figure 4:
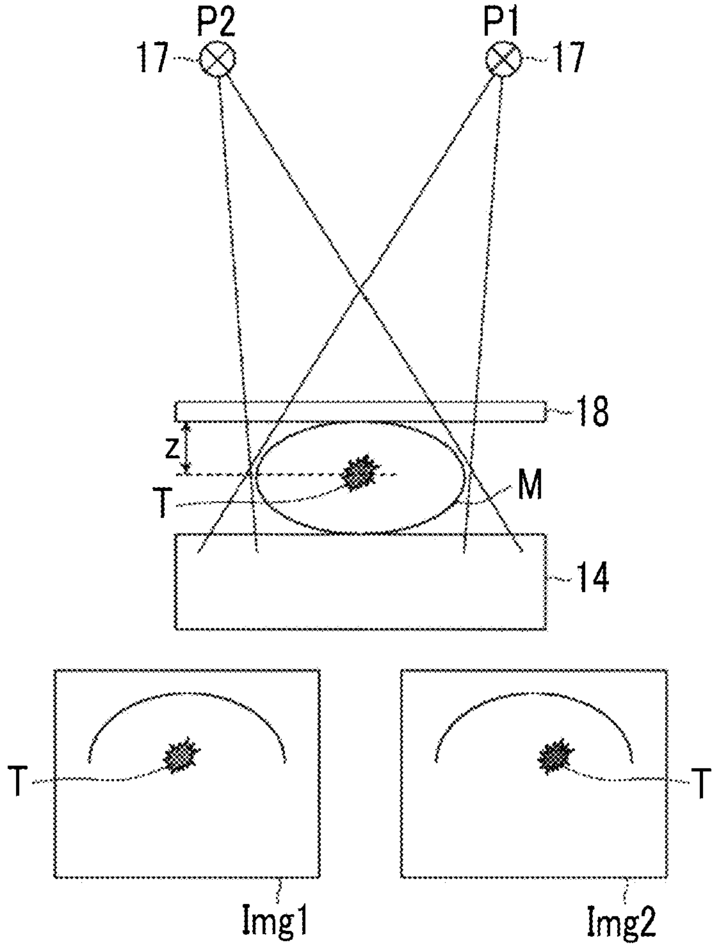
FIG. 4 is a diagram illustrating an example of a relationship between positions of a radiation irradiator in the mammography apparatus according to the embodiment and two scout images.

FIG. 4 is a diagram illustrating an example of a relationship between the positions of the radiation irradiator 17 and two scout images. In a scout image Img1 obtained by performing imaging in a state where the radiation irradiator 17 is placed at a position P1, a position of a target T appears to be close to the left side, and in a scout image Img2 obtained by performing imaging in a state where the radiation irradiator 17 is placed at a position P2, a position of a target T appears to be close to the right side. From the deviation of the target T between the two scout images Img1 and Img2, a distance z from a bottom surface of the compression plate 18 (the side that presses the breast) to the target T and the position of the target T on the XY plane are obtained, and thus, three-dimensional position information of the target T can be obtained.

In addition, the mammography apparatus 2 can perform stereo imaging. In the stereo imaging, radiation is emitted from each of two irradiation positions having different irradiation angles toward the breast by the radiation irradiator 17, and two radiation images of the breast are imaged. That is, in the stereo imaging, the imaging is performed while the angles of the imaging table 14, the compression plate 18, the breast, and the like are fixed and the rotation angle of the radiation irradiator 17 with respect to the base 11 is changed.

Further, the mammography apparatus 2 can perform tomosynthesis imaging. In the tomosynthesis imaging, radiation is emitted from each of a plurality of irradiation positions having different irradiation angles toward the breast by the radiation irradiator 17, and a plurality of radiation images of the breast are imaged. That is, even in the tomosynthesis imaging, the imaging is performed while the angles of the imaging table 14, the compression plate 18, the breast, and the like are fixed and the rotation angle of the radiation irradiator 17 with respect to the base 11 is changed.

Therefore, in the mammography apparatus 2 according to the present embodiment, by using the arm 13, it possible to change a relative angle (hereinafter, simply referred to as a "relative angle") between the radiation irradiator 17 and the imaging surface of the imaging table 14.

In a case where the needle position controller 35 of the biopsy unit 26 receives the position information of the target T, the needle position controller 35 moves the position of the distal end of the biopsy needle 21 to the position of the target T, and performs a puncture on the breast with the biopsy needle 21.

Figure 5:
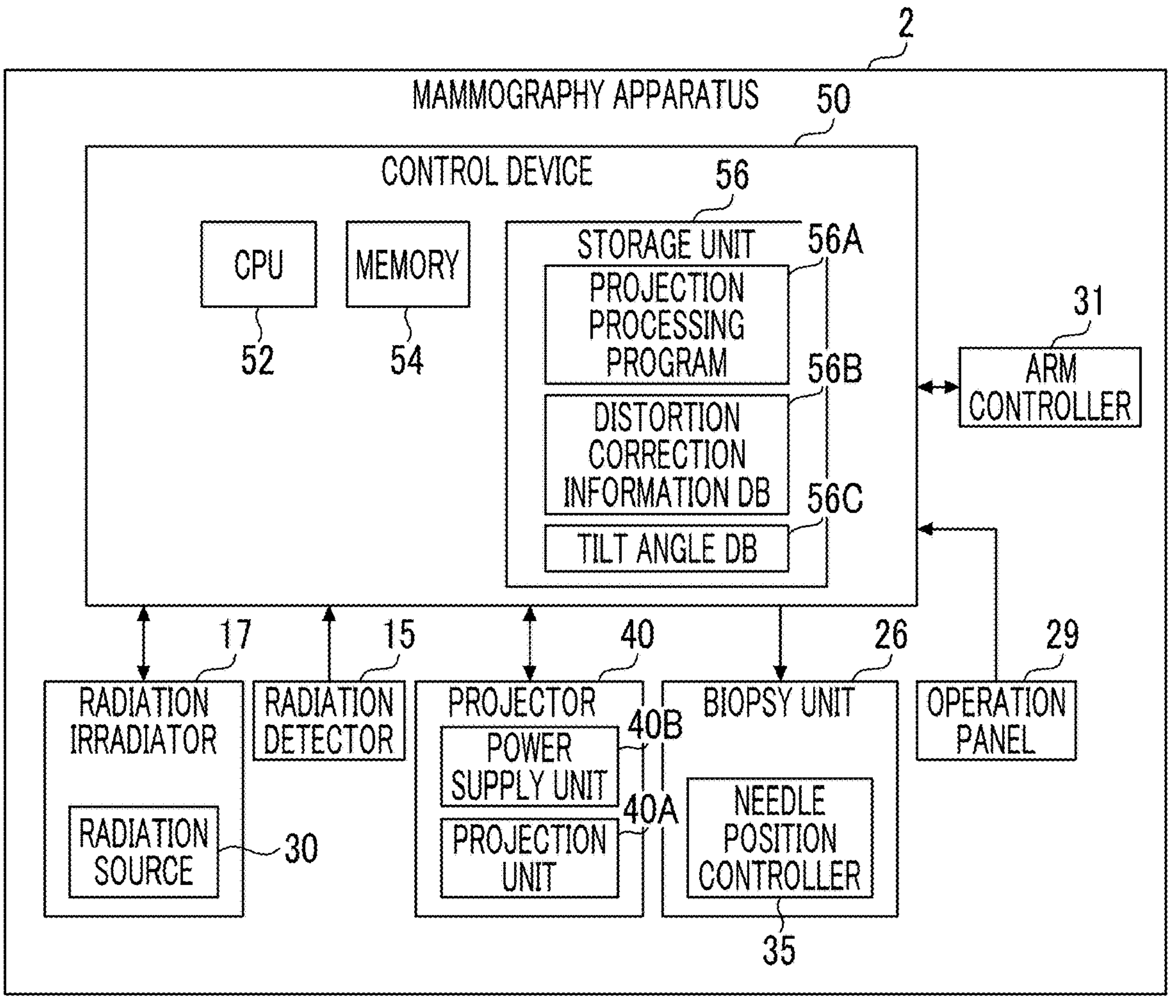
FIG. 5 is a block diagram illustrating an example of an electrical configuration of the mammography apparatus according to the embodiment.

Next, an electrical configuration of the mammography apparatus 2 according to the present embodiment will be described with reference to FIG. 5. FIG. 5 is a block diagram illustrating an example of the electrical configuration of the mammography apparatus according to the present embodiment.

The mammography apparatus 2 according to the present embodiment includes an operation panel 29 and a control device 50 in addition to the radiation detector 15, the radiation irradiator 17, the biopsy unit 26, the arm controller 31, and the projector 40.

The control device 50 has functions to control the entire operation of the mammography apparatus 2, and comprises a central processing unit (CPU) 52 as a processor, a memory 54 including a read only memory (ROM) and a random access memory (RAM), and a nonvolatile storage unit 56 including a hard disk drive (HDD), a flash memory, and the like. In addition, the control device 50 is connected to the radiation irradiator 17, the radiation detector 15, the biopsy unit 26, the arm controller 31, the projector 40, and the operation panel 29.

In a case where the control device 50 receives an irradiation instruction from the operator via the operation panel 29 (exposure switch), the control device 50 causes a radiation source 30 provided in the radiation irradiator 17 to irradiate an upper surface of the imaging table 14 with radiation according to an imaging menu which is set based on a designated exposure condition.

The radiation detector 15 receives irradiation of radiation carrying image information and records the image information, and outputs the recorded image information. For example, the radiation detector 15 is configured as a flat panel detector (FPD) that includes a radiation-sensitive layer and converts radiation into digital data and outputs the digital data. In a case where the radiation detector 15 is irradiated with radiation, the radiation detector 15 outputs the image information indicating the radiation image to the control device 50. In the present embodiment, the radiation detector 15 receives irradiation of the radiation that has passed through a breast M, and thus, the image information indicating the radiation image is obtained.

The operation panel 29 has a function of setting various types of operation information such as exposure conditions and posture information, various operation instructions, and the like.

The exposure condition which is set via the operation panel 29 includes information such as a tube voltage, a tube current, and an irradiation time. The posture information designated via the operation panel 29 includes information representing an imaging position (an imaging posture and an angle) in a case of imaging the breast M from a plurality of directions.

Note that various types of operation information such as the exposure conditions and the posture information, various operation instructions, and the like may be set by the operator using the operation panel 29, may be obtained from another control device (a radiology information system (RIS), a radiation information system, or a system that manages information on medical treatment, diagnosis, and the like using radiation) or the like, or may be stored in advance in a storage unit.

In a case where various types of information are set via the operation panel 29, the control device 50 causes the radiation irradiator 17 to irradiate an imaging part (breast M) of a subject with radiation according to the imaging menu which is set based on the various types of set information, and performs imaging of a radiation image. In a case of performing tomosynthesis imaging in which imaging is performed from a plurality of directions, the control device 50 adjusts the posture of the arm 13 such that the radiation irradiator 17 is positioned above the upper surface of the imaging table 14. In addition, in a state substantially similar to the state illustrated in FIG. 3, the control device 50 causes the radiation source 30 provided in the radiation irradiator 17 to individually irradiate the upper surface of the imaging table 14 with radiation at different angles based on the imaging condition by rotating the arm 13 to move the radiation irradiator 17 in an arc shape from a predetermined initial angle by a predetermined interval angle. Thereby, a plurality of radiation images can be obtained.

The needle position controller 35 provided in the biopsy unit 26 drives the biopsy unit 26 to move the biopsy needle 21 to a predetermined position and holds the biopsy needle 21 in a state where the biopsy needle 21 is tilted to an insertion angle, in response to the instruction from the control device 50.

As illustrated in FIG. 1 and FIG. 3, the biopsy unit 26 according to the present embodiment can perform not only a longitudinal puncture in which the puncture direction of the biopsy needle 21 is perpendicular to the imaging surface of the imaging table 14 but also a lateral puncture in which the puncture direction of the biopsy needle 21 is parallel to the imaging surface of the imaging table 14. On the other hand, the present disclosure is not limited thereto. For example, a form in which the biopsy unit 26 can perform only a longitudinal puncture may be adopted.

The projector 40 according to the present embodiment includes a projection unit 40A and a power supply unit 40B. In the projector 40, the power supply unit 40B is controlled to be turned on and off in response to an instruction of the control device 50. In addition, the projection image is projected from the projection unit 40A toward the upper surface of the compression plate 18 in response to an instruction of the control device 50.

Further, in a case of performing imaging of the scout image, the stereo imaging, and the tomosynthesis imaging as described above, the control device 50 controls the arm controller 31 such that the rotation angle of the arm 13 is an angle corresponding to the imaging.

Further, a projection processing program 56A is stored in the storage unit 56 as a storage medium provided in the control device 50 according to the present embodiment. The CPU 52 reads out the projection processing program 56A from the storage unit 56, develops the read-out projection processing program 56A in the memory 54, and executes the developed projection processing program 56A. In addition, the storage unit 56 stores a distortion correction information database 56B and a tilt angle database 56C. Details of these databases will be described later.

Figure 6:
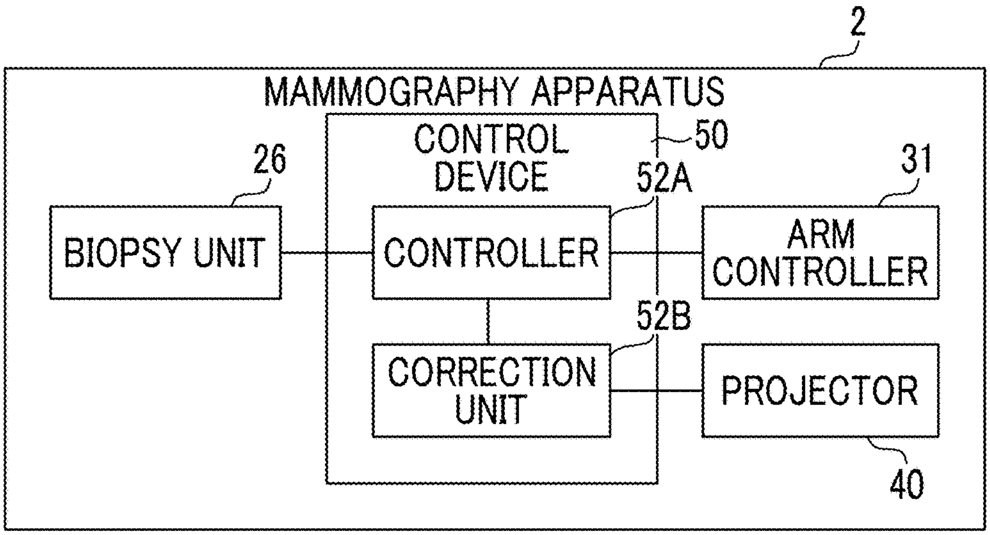
FIG. 6 is a functional block diagram illustrating a functional configuration of a control device provided in the mammography apparatus according to the embodiment.

Next, a functional configuration of the control device 50 according to the present embodiment will be described with reference to FIG. 6. FIG. 6 is a functional block diagram illustrating a functional configuration of the control device 50 provided in the mammography apparatus 2 according to the present embodiment.

As illustrated in FIG. 6, the control device 50 includes a controller 52A and a correction unit 52B. In a case where the CPU 52 executes the projection processing program 56A, the control device 50 functions as the controller 52A and the correction unit 52B.

The controller 52A according to the present embodiment controls the arm 13 such that the relative angle is a predetermined tilt angle in a case where a biopsy using the longitudinal puncture is performed by the biopsy unit 26.

In particular, in the present embodiment, in a case of performing the tilt imaging other than the imaging in which the imaging table 14, the radiation irradiator 17, and the biopsy unit 26 are arranged in a straight line, an angle according to the tilt imaging is applied as a tilt angle. In the present embodiment, both the stereo imaging and the tomosynthesis imaging are applied as the tilt imaging. On the other hand, the present disclosure is not limited thereto. A form in which only one of the stereo imaging or the tomosynthesis imaging is applied as the tilt imaging may be adopted.

In addition, the controller 52A according to the present embodiment performs a control of the arm 13 such that the relative angle is the tilt angle and the arm 13 is tilted toward a side away from the position of the operator who performs imaging of the radiation image (hereinafter, referred to as a "first control"). Further, the controller 52A according to the present embodiment performs a control of the arm 13 such that the relative angle is the tilt angle and the arm 13 is tilted toward a side opposite to the right-left direction of the breast for which the biopsy is to be performed (hereinafter, referred to as a "second control"). Note that the "side opposite to the right-left direction of the breast" means the right side in a case where the breast for which the biopsy is to be performed is the left breast and means the left side in a case where the breast for which the biopsy is to be performed is the right breast.

Here, the tilt direction of the arm 13 by the first control and the tilt direction of the arm 13 by the second control may be different from each other. In this case, the controller 52A controls the arm 13 such that the arm 13 is tilted toward the side away from the position of the operator with priority given to the first control. On the other hand, the present disclosure is not limited to this form. A form in which the priority of the second control is set to be higher than the priority of the first control may be adopted, or a form in which the priorities of the first control and the second control are appropriately switched in accordance with a situation of the subject, the purpose of performing the biopsy, or the like may be adopted.

On the other hand, the correction unit 52B according to the present embodiment corrects a distortion of the projection image by the projector 40, the distortion occurring in a case where the relative angle is set to the tilt angle. Note that, in the present embodiment, as a method of correcting the distortion of the projection image, a method of using a coordinate conversion table that can convert the projection image into an image without distortion as a result in a case where the projection image is projected onto the upper surface of the compression plate 18 is applied. In the present embodiment, a method of preparing the coordinate conversion table in advance for each predetermined interval angle (in the present embodiment, 2 degrees) of the tilt angle and correcting the distortion by selectively applying the coordinate conversion table corresponding to the nearest tilt angle is used. On the other hand, the present disclosure is not limited thereto. For example, a form in which a method of using, instead of the coordinate conversion table, a coordinate conversion expression that can convert the projection image into an image without distortion as a result in a case where the projection image is projected onto the upper surface of the compression plate 18 is applied as a method of correcting the distortion of the projection image may be adopted. In addition, the present disclosure is not limited to the method using the coordinate conversion table or the coordinate conversion expression. A form in which a known algorithm in the related art, such as projection conversion which is intended to correct a distortion of an image, is applied as a method of correcting a distortion of a projection image may be adopted.

As described above, the mammography apparatus 2 according to the present embodiment comprises the control device 50 therein. However, the present disclosure is not limited thereto. For example, the control device 50 may be configured as a device separated from the mammography apparatus 2. The control device 50 according to the present embodiment corresponds to a control device according to the technology of the present disclosure.

In addition, as described above, in a case where the biopsy using the longitudinal puncture is performed by the biopsy unit 26, the controller 52A according to the present embodiment controls the arm 13 such that the relative angle is a predetermined tilt angle. On the other hand, the purpose of the control is to avoid or prevent the biopsy unit 26 from interfering with the projection region obtained by the projector 40.

Therefore, in a case where the biopsy unit 26 interferes with the projection region obtained by the projector 40, a form may be adopted in which the controller 52A according to the present embodiment controls the arm 13 such that the relative angle is a predetermined angle as an angle at which a light shielding region that is caused by the biopsy unit 26 and is included in the projection image obtained by the projector 40 has an area equal to or smaller than a predetermined area. In this form, the predetermined area is most preferably 0 (zero). On the other hand, an effect of improving the visibility of the projection image can be obtained even in a case where a part of the projection image is outside the light shielding region.

Next, the distortion correction information database 56B according to the present embodiment will be described with reference to FIG. 7. FIG. 7 is a schematic diagram illustrating an example of a configuration of a distortion correction information database 56B according to the present embodiment.

The distortion correction information database 56B according to the present embodiment is a database in which the above-described coordinate conversion table is registered. As illustrated in FIG. 7, the distortion correction information database 56B according to the present embodiment stores the tilt angle and information of each of the coordinate conversion tables.

The tilt angle is information indicating the above-described tilt angle itself, and the coordinate conversion table is information indicating the above-described coordinate conversion table itself corresponding to the tilt angle.

Next, the tilt angle database 56C according to the present embodiment will be described with reference to FIG. 8. FIG. 8 is a schematic diagram illustrating an example of a configuration of the tilt angle database 56C according to the present embodiment.

As illustrated in FIG. 8, the tilt angle database 56C according to the present embodiment stores information of each of the imaging condition and the tilt angle.

The imaging condition is information indicating a difference between the stereo imaging and the tomosynthesis imaging described above, and the tilt angle is information indicating the tilt angle itself to be applied in a case of performing imaging under the corresponding imaging condition.

In the example illustrated in FIG. 8, for example, in a case of performing the stereo imaging, information indicating that −15 degrees or +15 degrees is applied as the tilt angle is registered, and in a case of performing the tomosynthesis imaging, information indicating that −20 degrees or +20 degrees is applied as the tilt angle is registered.

Figure 9:
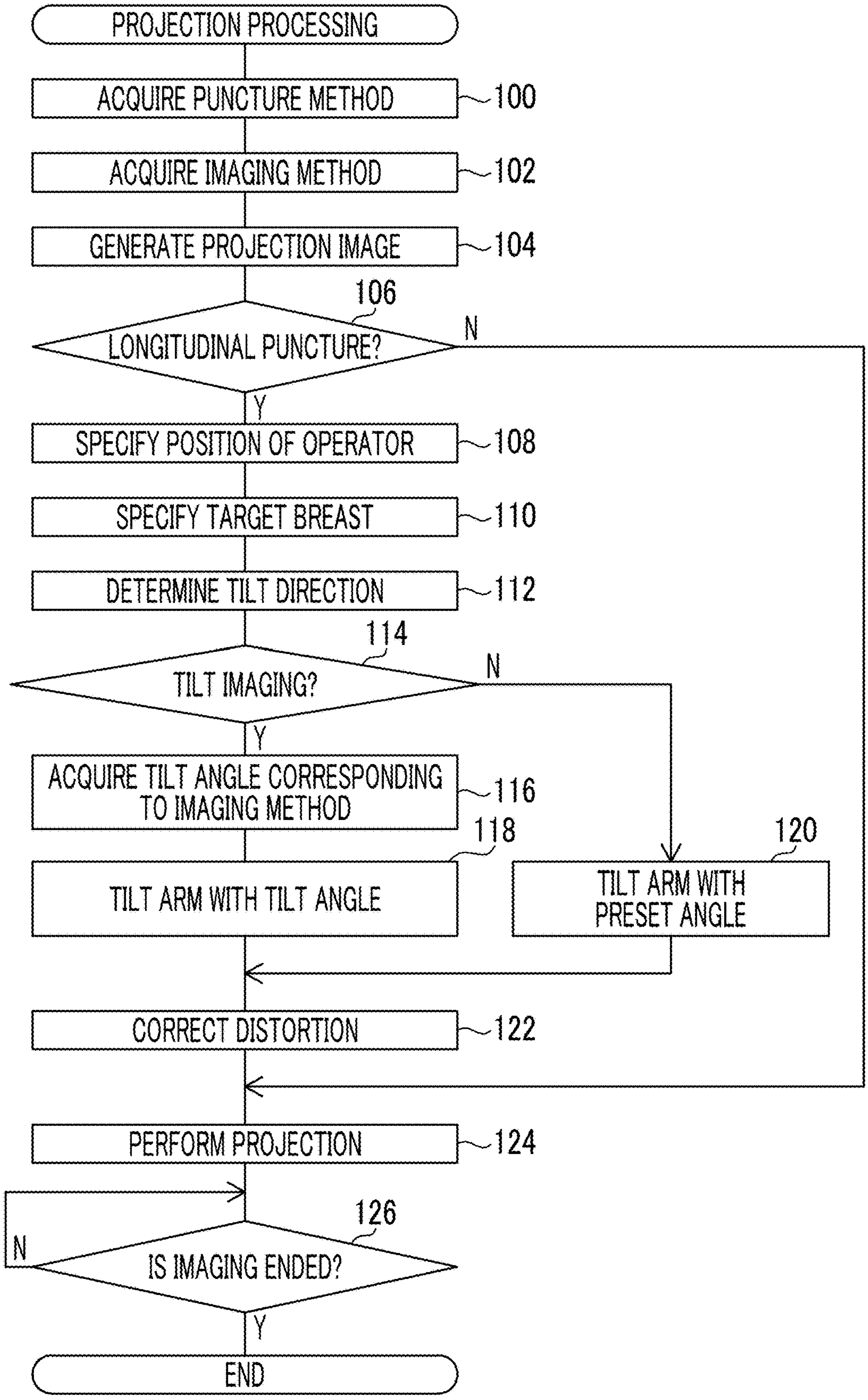
FIG. 9 is a flowchart illustrating an example of projection processing according to the embodiment.

Next, an operation of the mammography apparatus 2 according to the present embodiment in a case of performing projection processing will be described with reference to FIG. 9, the projection processing being processing of projecting a projection image onto the upper surface of the compression plate 18 by the projector 40. In a case where the CPU 52 of the control device 50 of the mammography apparatus 2 executes the projection processing program 56A, projection processing illustrated in FIG. 9 is executed. The projection processing illustrated in FIG. 9 is executed, for example, in a case where the mammography apparatus 2 performs radiography while biopsy examination by the biopsy unit 26 is performed. Note that, in order to avoid confusion, here, a case where the distortion correction information database 56B and the tilt angle database 56C are already constructed will be described. In addition, here, a case where puncture method information indicating whether the puncture method to be applied in the biopsy examination is a longitudinal puncture or a lateral puncture is already registered will be described. Further, here, a case where imaging method information indicating that any of the imaging in a state where the imaging table 14, the radiation irradiator 17, and the biopsy unit 26 are arranged in a straight line (hereinafter, referred to as "serial imaging"), the stereo imaging, and the tomosynthesis imaging is to be performed is already registered will be described.

In step 100 of FIG. 9, the CPU 52 acquires the above-described puncture method information, and in step 102, the CPU 52 acquires the above-described imaging method information.

In step 104, the CPU 52 generates image information indicating a projection image to be projected by the projector 40 (hereinafter, referred to as "projection image information"). Here, the CPU 52 generates projection image information that displays information indicating a puncture position, a target, or the like, which is useful when being displayed at this time.

In step 106, the CPU 52 determines whether or not the acquired puncture method information indicates to apply the longitudinal puncture. In a case where a determination result in step 106 is "No", the CPU 52 proceeds to step 124. In a case where a determination result in step 106 is "Yes", the CPU 52 proceeds to step 108.

In step 108, the CPU 52 specifies a position of an operator (hereinafter, simply referred to as an "operator") of the mammography apparatus 2. In the present embodiment, an imaging device that performs imaging using visible light is provided in the vicinity of the mammography apparatus 2. In the imaging device, a region in which an operator may be present during the operation of the mammography apparatus 2 is set as an imaging range. The position of the operator is specified from image information obtained by the imaging performed by the imaging device. On the other hand, the present disclosure is not limited to this form, and for example, a method using a person detection sensor may be applied as a method of specifying the position of the operator.

In step 110, the CPU 52 specifies the right-left direction of the target breast. In the present embodiment, the right-left direction is specified by inputting the right-left direction through the operation panel 29 by the operator. On the other hand, the present disclosure is not limited thereto.

In step 112, the CPU 52 determines the tilt direction of the arm 13 as described above by using the position of the operator and the right-left direction of the target breast that are specified by the above processing.

In step 114, the CPU 52 determines whether or not the acquired imaging method information indicates that the stereo imaging or the tomosynthesis imaging is to be performed, that is, whether or not the tilt imaging is to be performed, and in a case where a determination result is YES, the CPU 52 proceeds to step 116.

In step 116, the CPU 52 reads out the information indicating the tilt angle corresponding to the imaging method from the tilt angle database 56C. In step 118, the CPU 52 controls the arm controller 31 such that the relative angle with respect to the determined tilt direction is the read-out tilt angle, and then proceeds to step 122.

On the other hand, in a case where a determination result in step 114 is NO, the CPU 52 proceeds to step 120 on an assumption that the above-described serial imaging is to be performed. In step 120, the CPU 52 controls the arm controller 31 such that the relative angle with respect to the determined tilt direction is a preset tilt angle (in the present embodiment, 10 degrees), and then proceeds to step 122. In the present embodiment, the operator sets the tilt angle to be applied in step 120. On the other hand, it goes without saying that the present disclosure is not limited thereto.

In step 122, the CPU 52 reads out the coordinate conversion table corresponding to the tilt direction of the arm 13 at this time and corresponding to the tilt angle closest to the tilt angle at this time from the distortion correction information database 56B. In addition, the CPU 52 performs distortion correction on the projection image by performing coordinate conversion on the generated projection image information using the read-out coordinate conversion table.

In step 124, the CPU 52 controls the projector 40 to project the projection image by using the projection image information obtained by performing the above processing.

Thereafter, the mammography apparatus 2 performs any of the stereo imaging, the tomosynthesis imaging, or the serial imaging that is scheduled. Further, in step 126, the CPU 52 waits until any of the imaging is ended, and then ends the present projection processing.

Figure 10A:
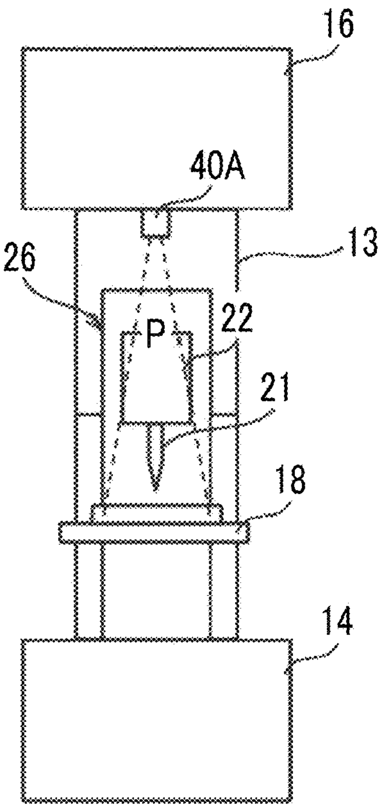
FIG. 10A is a diagram illustrating projection processing according to the embodiment, and is a front view illustrating a position relationship between main parts in a case of performing serial imaging.

FIG. 10A is a diagram illustrating the projection processing according to the present embodiment, and is a front view illustrating a position relationship between main parts in a case of performing the serial imaging. In addition, FIG. 10B is a diagram illustrating the projection processing according to the present embodiment, and is a front view illustrating a position relationship between main parts in a case where the relative angle with respect to the imaging surface of the arm is the tilt angle.

As illustrated in FIG. 10A, in a case of performing the serial imaging, when performing the longitudinal puncture, the parts, such as the biopsy needle unit 22 of the biopsy unit 26 that includes the biopsy needle 21 and a holder or the like which holds the biopsy needle 21, the moving mechanism 24 that moves the biopsy needle unit 22, and the like, are disposed immediately above the breast. For this reason, depending on the position of each of the above parts, the projection image P from the projector 40 may be shielded, and in this case, there is a problem that the visibility of the projection image is deteriorated. Note that, in the example illustrated in FIG. 10A, a case of performing the serial imaging is illustrated. On the other hand, this problem is a problem that may also occur in a case of performing the tilt imaging.

Figure 10B:
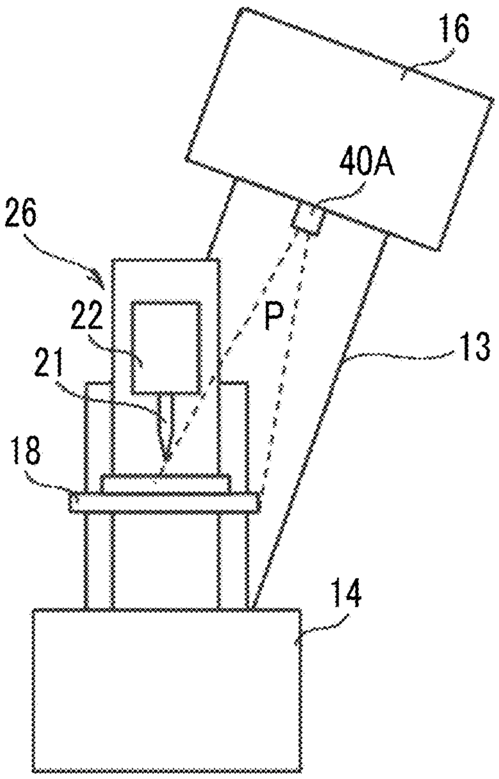
FIG. 10B is a diagram illustrating projection processing according to the embodiment, and is a front view illustrating a position relationship between main parts in a case where a relative angle with respect to an imaging surface of an arm is a tilt angle.

Therefore, in the present embodiment, as illustrated in FIG. 10B as an example, the arm 13 is controlled such that the relative angle is the tilt angle regardless of the tilt imaging or the serial imaging. By this control, a region where the projection image P is shielded by each of the parts can be eliminated or at least narrowed. As a result, the visibility of the projection image can be improved as compared with the related art.

As described above, according to the present embodiment, in a case where the biopsy using the longitudinal puncture is performed by the biopsy unit 26, the arm 13 is controlled such that the relative angle is a predetermined tilt angle. Therefore, the visibility of the projection image can be improved as compared with the related art.

In addition, according to the present embodiment, in a case of performing the tilt imaging other than the imaging in which the imaging table 14, the radiation irradiator 17, and the biopsy unit 26 are arranged in a straight line, that is, the serial imaging, the predetermined tilt angle is set as an angle according to the tilt imaging. Therefore, it is possible to promptly execute the tilt imaging after the projection of the projection image.

Further, according to the present embodiment, the stereo imaging and the tomosynthesis imaging are applied as the tilt imaging. Therefore, it is possible to quickly switch to the stereo imaging or the tomosynthesis imaging after the projection of the projection image.

In addition, according to the present embodiment, the arm 13 is controlled such that the relative angle is the predetermined tilt angle and the arm 13 is tilted to the side away from the position of the operator who performs the imaging of the radiation image. Therefore, it is possible to improve the operability of the mammography apparatus 2 by the operator.

Further, according to the present embodiment, the arm 13 is controlled such that the relative angle is the predetermined tilt angle and the arm 13 is tilted toward the side opposite to the right-left direction of the breast for which the biopsy is to be performed. Therefore, it is possible to secure a region for the operation of the mammography apparatus 2 by the operator, and thus it is possible to improve the operability of the mammography apparatus 2 by the operator.

In addition, according to the present embodiment, in a case where the side away from the position of the operator and the side opposite to the right-left direction of the breast are different sides when controlling the tilt direction of the arm 13, the arm 13 is controlled to be tilted toward the side away from the position of the operator. Therefore, it is possible to more reliably improve the operability of the mammography apparatus 2 by the operator.

In addition, according to the present embodiment, the distortion of the projection image obtained by the projector 40 that occurs in a case where the relative angle is set to the tilt angle is corrected. Therefore, the visibility of the projection image can be further improved.

Further, according to the present embodiment, in a case where the biopsy using the longitudinal puncture is performed by the biopsy unit 26, when performing the serial imaging, the arm 13 is controlled such that the relative angle is a preset tilt angle. Therefore, the visibility of the projection image can be improved as compared with the related art.

Note that, in the embodiment, the drive position of the biopsy unit 26 and the position of the compression plate 18 are not considered. On the other hand, a form in which at least one of the relative angle or the projection position of the projection image obtained by the projector 40 is adjusted according to the drive position of the biopsy unit 26 may be adopted. In addition, a form in which the relative angle is adjusted according to the position of the compression plate 18 may be adopted. Hereinafter, these forms will be specifically described.

Figure 11A:
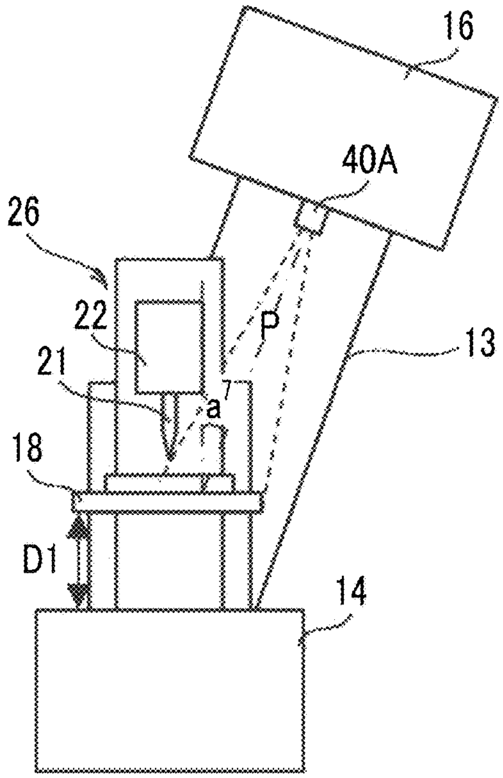
FIG. 11A is a diagram illustrating a modification example of the projection processing according to the embodiment, and is a front view illustrating a position relationship between main parts in a case where a height of a compression plate is a height D1.

First, an example of a form in a case where the relative angle is adjusted according to the position of the compression plate 18 will be described with reference to FIG. 11A and FIG. 11B. FIG. 11A is a diagram illustrating a modification example of the projection processing according to the present embodiment, and is a front view illustrating a position relationship between main parts in a case where the height of the compression plate 18 is a height D1. Further, FIG. 11B is a diagram illustrating a modification example of the projection processing according to the present embodiment, and is a front view illustrating a position relationship between main parts in a case where the height of the compression plate 18 is a height D2 lower than the height D1.

Figure 11B:
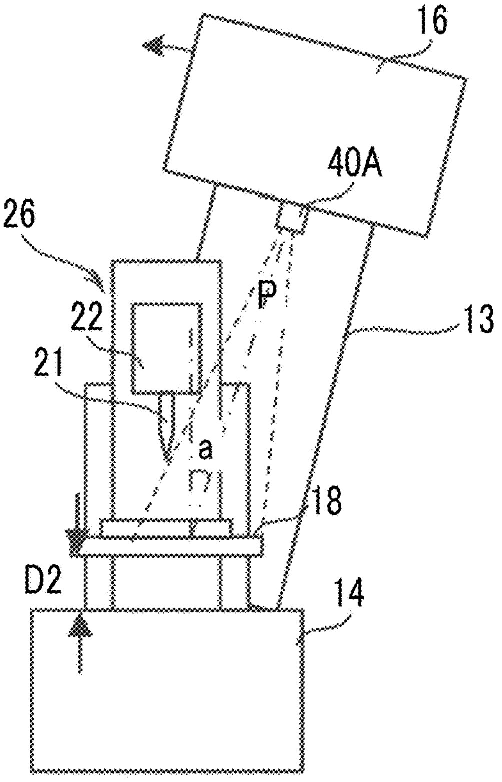
FIG. 11B is a diagram illustrating a modification example of the projection processing according to the embodiment, and is a front view illustrating a position relationship between main parts in a case where a height of a compression plate is a height D2 lower than the height D1.

As illustrated in FIG. 11A and FIG. 11B, in a case where the height of the compression plate 18 is the height D2, as compared with a case where the height of the compression plate 18 is the height D1, it is possible to avoid each part of the biopsy unit 26 from shielding the projection image even though the relative angle a is a small angle. On the other hand, as the relative angle a is smaller, an amount of the distortion of the projection image is reduced.

Therefore, in the present modification example, the arm 13 is controlled such that the relative angle a is smaller as the height of the compression plate 18 is lower. By this control, it is possible to achieve both improvement of the visibility of the projection image and reduction of the distortion.

Figure 12A:
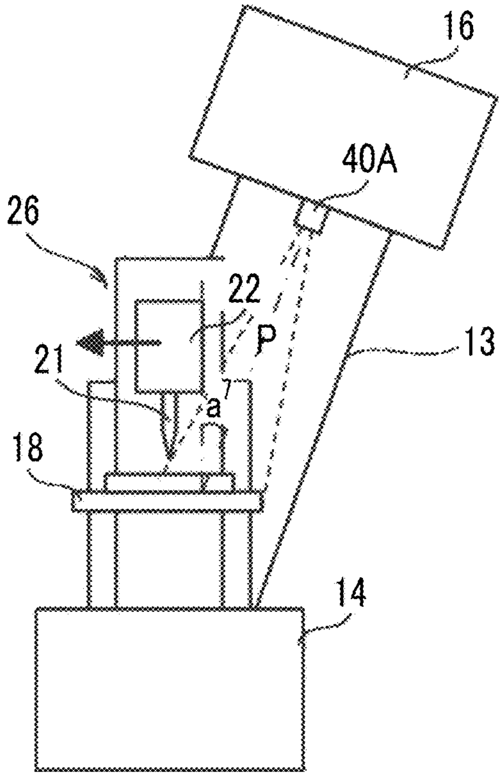
FIG. 12A is a diagram illustrating a modification example of the projection processing according to the embodiment, and is a front view illustrating a position relationship between main parts in a case where a biopsy device is positioned at the center.

Next, an example of a form in a case where the relative angle is adjusted according to the drive position of the biopsy unit 26 will be described with reference to FIG. 12A and FIG. 12B. FIG. 12A is a diagram illustrating a modification example of the projection processing according to the present embodiment, and is a front view illustrating a position relationship between main parts in a case where the biopsy device is positioned at the center. Further, FIG. 12B is a diagram illustrating a modification example of the projection processing according to the present embodiment, and is a front view illustrating a position relationship between main parts in a case where the biopsy device is positioned on the left side from the center.

Figure 12B:
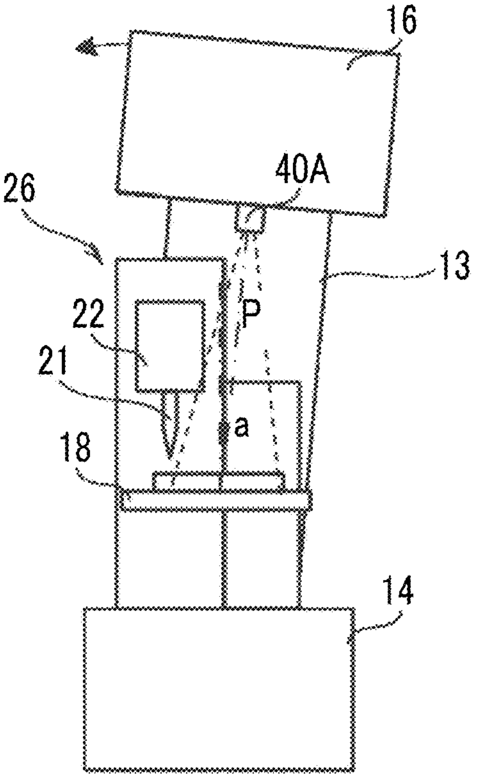
FIG. 12B is a diagram illustrating a modification example of the projection processing according to the embodiment, and is a front view illustrating a position relationship between main parts in a case where a biopsy device is positioned on a left side from the center.

As illustrated in FIG. 12A and FIG. 12B, in a case where the drive position of the biopsy unit 26 is shifted in the right-left direction, as compared with a case where the biopsy unit 26 is positioned at the center, it is possible to avoid each part of the biopsy unit 26 from shielding the projection image even though the relative angle a is a small angle. On the other hand, as described above, as the relative angle a is smaller, an amount of the distortion of the projection image is reduced.

Therefore, in the present modification example, the arm 13 is controlled such that the relative angle a is smaller as the drive position of the biopsy unit 26 is shifted from the center. Even with this control, it is possible to achieve both improvement of the visibility of the projection image and reduction of the distortion.

Figure 13A:
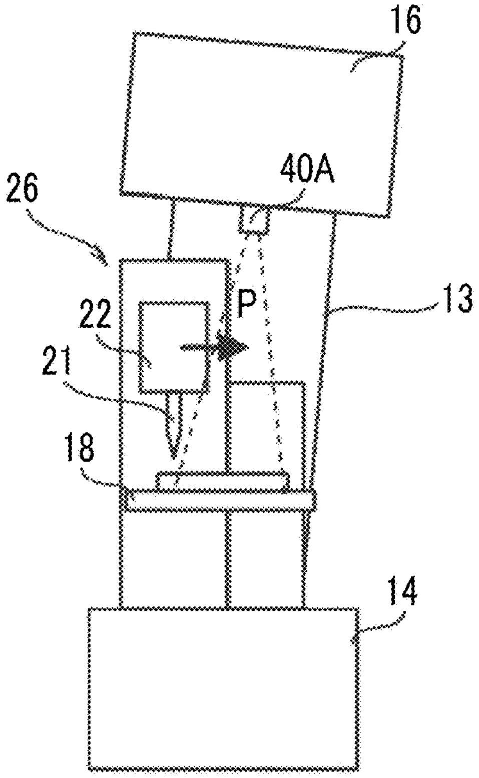
FIG. 13A is a diagram illustrating a modification example of the projection processing according to the embodiment, and is a front view illustrating a position relationship between main parts in a case where a biopsy device is positioned on a left side from the center.

Further, an example of a form in a case where the projection position of the projection image is adjusted according to the drive position of the biopsy unit 26 will be described with reference to FIG. 13A and FIG. 13B. FIG. 13A is a diagram illustrating a modification example of the projection processing according to the present embodiment, and is a front view illustrating a position relationship between main parts in a case where the biopsy device is positioned on the left side from the center. In addition, FIG. 13B is a diagram illustrating a modification example of the projection processing according to the present embodiment, and is a front view illustrating a position relationship between main parts in a case where the biopsy device is positioned at the center.

Figure 13B:
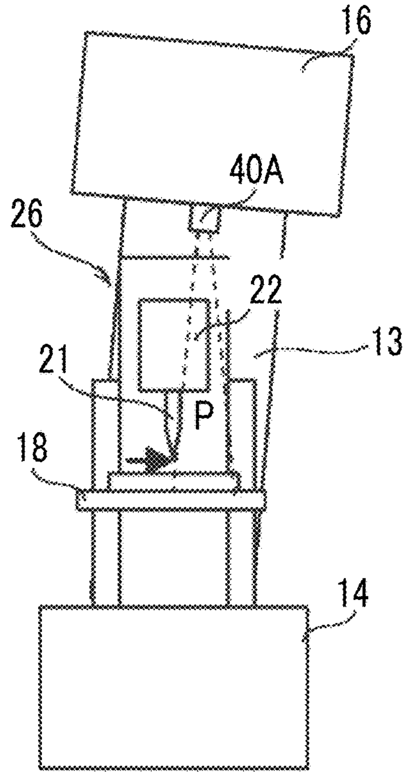
FIG. 13B is a diagram illustrating a modification example of the projection processing according to the embodiment, and is a front view illustrating a position relationship between main parts in a case where a biopsy device is positioned at the center.

As illustrated in FIG. 13A and FIG. 13B, in a case where the drive position of the biopsy unit 26 is located at the center, as compared with a case where the drive position of the biopsy unit 26 is shifted in the right-left direction, a shielded region of the projection image by the biopsy unit 26 is wider. On the other hand, as described above, as the relative angle a is smaller, an amount of the distortion of the projection image is reduced.

Therefore, in this modification example, control is performed such that the projection position of the projection image is adjusted to be shifted in the right-left direction as the drive position of the biopsy unit 26 is closer to the center after the relative angle a is fixed to a relatively small tilt angle. Even with this control, it is possible to achieve both improvement of the visibility of the projection image and reduction of the distortion.

Further, in the embodiment, the case where the relative angle in the serial imaging is set to the preset tilt angle has been described. On the other hand, the present disclosure is not limited thereto. For example, a form in which the relative angle is set to a preset tilt angle regardless of the imaging method may be adopted.

Further, in the above embodiment, the case where the CPU 52 provided in the control device 50 of the mammography apparatus 2 is applied as a processor of the technology of the present disclosure has been described. On the other hand, the present disclosure is not limited thereto. For example, the needle position controller 35 of the biopsy unit 26 may be applied as a processor of the technology of the present disclosure.

In the above embodiment, for example, as a hardware structure of a processing unit that executes various types of processing, such as the controller 52A and the correction unit 52B, the following various processors can be used. As described above, the various processors include, in addition to the CPU that is a general-purpose processor that executes software (program) to function as various processing units, a programmable logic device (PLD) that is a processor of which a circuit configuration can be changed after manufacture, such as a field programmable gate array (FPGA), and a dedicated electric circuit that is a processor having a circuit configuration that is designed for exclusive use in order to execute a specific process, such as an application specific integrated circuit (ASIC).

One processing unit may be configured by one of the various processors, or may be configured by a combination of the same or different types of two or more processors (for example, a combination of a plurality of FPGAs or a combination of the CPU and the FPGA). In addition, a plurality of processing units may be configured by one processor.

As an example in which the plurality of processing units are configured by one processor, firstly, as represented by a computer such as a client and a server, a form in which one processor is configured by a combination of one or more CPUs and software and the processor functions as the plurality of processing units may be adopted. Secondly, as represented by a system on chip (SoC) or the like, a form in which a processor that realizes the function of the entire system including the plurality of processing units by one integrated circuit (IC) chip is used may be adopted. In this manner, the various processing units are configured by using one or more various processors as a hardware structure.

Furthermore, as the hardware structure of the various processors, more specifically, an electrical circuit (circuitry) in which circuit elements such as semiconductor elements are combined can be used.

In addition, in the above embodiment, the form in which the projection processing program 56A is stored (installed) in advance in the storage unit 56 of the mammography apparatus 2 has been described. On the other hand, the present disclosure is not limited thereto. The projection processing program 56A may be provided by being recorded in a recording medium, such as a compact disc read only memory (CD-ROM), a digital versatile disc read only memory (DVD-ROM), or a universal serial bus (USB) memory. In addition, the projection processing program 56A may be downloaded from an external device through a network.

From the above description, the invention described in following Appendices can be understood.

APPENDIX 1

A mammography apparatus including a biopsy device, an imaging table, and an arm in which a radiation irradiator and a projector are provided on one end portion side and a relative angle between the radiation irradiator and an imaging surface of the imaging table is changeable, the radiation irradiator emitting radiation for imaging of a radiation image toward the imaging surface of the imaging table, the mammography apparatus comprising:

at least one processor, in which the processor is configured to control the arm such that the relative angle is a predetermined tilt angle in a case where biopsy using a longitudinal puncture is performed by the biopsy device.

APPENDIX 2

The mammography apparatus according to Appendix 1, in which, in a case of performing tilt imaging other than imaging in which the imaging table, the radiation irradiator, and the biopsy device are arranged in a straight line, the predetermined tilt angle is an angle according to the tilt imaging.

APPENDIX 3

The mammography apparatus according to Appendix 2, in which the tilt imaging is imaging of at least one of stereo imaging or tomosynthesis imaging.

APPENDIX 4

The mammography apparatus according to any one of Appendixes 1 to 3, in which the processor is configured to control the arm such that the relative angle is the predetermined tilt angle and the arm is tilted toward a side away from a position of an operator who performs imaging of the radiation image.

APPENDIX 5

The mammography apparatus according to any one of Appendixes 1 to 3, in which the processor is configured to control the arm such that the relative angle is the predetermined tilt angle and the arm is tilted toward a side opposite to a right-left direction of a breast for which the biopsy is to be performed.

APPENDIX 6

The mammography apparatus according to any one of Appendixes 1 to 3, in which, in a case where the processor is configured to:

control the arm such that the relative angle is the predetermined tilt angle and the arm is tilted toward a side away from a position of an operator who performs imaging of the radiation image; and control the arm such that the relative angle is the predetermined tilt angle and the arm is tilted toward a side opposite to a right-left direction of a breast for which the biopsy is to be performed, the processor is configured to control the arm such that the arm is tilted toward a side away from the position of the operator in a case where the side away from the position of the operator and the side opposite to the right-left direction of the breast are different from each other.

APPENDIX 7

The mammography apparatus according to any one of Appendixes 1 to 6, in which the processor is configured to adjust the relative angle according to a drive position of the biopsy device.

APPENDIX 8

The mammography apparatus according to any one of Appendixes 1 to 7, in which the processor is configured to adjust a projection position of a projection image by the projector according to a drive position of the biopsy device.

APPENDIX 9

The mammography apparatus according to any one of Appendixes 1 to 8, in which the processor is configured to adjust the relative angle according to a position of a compression plate provided on the imaging surface side of the imaging table.

APPENDIX 10

The mammography apparatus according to any one of Appendixes 1 to 9, in which the processor is configured to correct a distortion of a projection image that is caused by the projector and occurs in a case where the relative angle is set to the tilt angle.

APPENDIX 11

The mammography apparatus according to Appendix 1, in which the processor is configured to control the arm such that the relative angle is a preset tilt angle regardless of an imaging condition in a case where biopsy using a longitudinal puncture is performed by the biopsy device.

APPENDIX 12

A control device that controls a mammography apparatus, the mammography apparatus including a biopsy device, an imaging table, and an arm in which a radiation irradiator and a projector are provided on one end portion side and a relative angle between the radiation irradiator and an imaging surface of the imaging table is changeable, the radiation irradiator emitting radiation for imaging of a radiation image toward the imaging surface of the imaging table, the control device comprising:

at least one processor, in which the processor is configured to control the arm such that the relative angle is a predetermined angle in a case where the biopsy device interferes with a projection region by the projector, the predetermined angle being an angle at which a light shielding region by the biopsy device that is included in a projection image by the projector has an area equal to or smaller than a predetermined area.

APPENDIX 13

A program to be executed in a mammography apparatus, the mammography apparatus including a biopsy device, an imaging table, and an arm in which a radiation irradiator and a projector are provided on one end portion side and a relative angle between the radiation irradiator and an imaging surface of the imaging table is changeable, the radiation irradiator emitting radiation for imaging of a radiation image toward the imaging surface of the imaging table, the program causing a computer to execute a process comprising:

controlling the arm such that the relative angle is a predetermined tilt angle in a case where biopsy using a longitudinal puncture is performed by the biopsy device.

APPENDIX 14

A program to be executed in a control device that controls a mammography apparatus, the mammography apparatus including a biopsy device, an imaging table, and an arm in which a radiation irradiator and a projector are provided on one end portion side and a relative angle between the radiation irradiator and an imaging surface of the imaging table is changeable, the radiation irradiator emitting radiation for imaging of a radiation image toward the imaging surface of the imaging table, the program causing a computer to execute a process comprising:

controlling the arm such that the relative angle is a predetermined angle in a case where the biopsy device interferes with a projection region by the projector, the predetermined angle being an angle at which a light shielding region by the biopsy device that is included in a projection image by the projector has an area equal to or smaller than a predetermined area.

What is claimed is:

1. A control device of a mammography apparatus including a biopsy device, an imaging table, and an arm in which a radiation irradiator and a projector are provided on one end portion side and a relative angle between the radiation irradiator and an imaging surface of the imaging table is changeable, the radiation irradiator emitting radiation for imaging of a radiation image toward the imaging surface of the imaging table, the control device comprising:

at least one processor that is configured to control the arm such that the relative angle is a predetermined tilt angle in a case where biopsy using a longitudinal puncture is performed by the biopsy device.

2. The control device according to claim 1, wherein, in a case of performing tilt imaging other than imaging in which the imaging table, the radiation irradiator, and the biopsy device are arranged in a straight line, the predetermined tilt angle is an angle according to the tilt imaging.

3. The control device according to claim 2, wherein the tilt imaging is imaging of at least one of stereo imaging or tomosynthesis imaging.

4. The control device according to claim 1, wherein the at least one processor is configured to control the arm such that the relative angle is the predetermined tilt angle and the arm is tilted toward a side away from a position of an operator who performs imaging of the radiation image.

5. The control device according to claim 1, wherein the at least one processor is configured to control the arm such that the relative angle is the predetermined tilt angle and the arm is tilted toward a side opposite to a right-left direction of a breast for which the biopsy is to be performed.

6. The control device according to claim 1, wherein, the at least one processor is configured to:

control the arm such that the relative angle is the predetermined tilt angle and the arm is tilted toward a side away from a position of an operator who performs imaging of the radiation image;

control the arm such that the relative angle is the predetermined tilt angle and the arm is tilted toward a side opposite to a right-left direction of a breast for which the biopsy is to be performed; and in a case in which the side away from the position of the operator and the side opposite to the right-left direction of the breast are different from each other, control the arm such that the arm is tilted toward the side away from the position of the operator.

7. The control device according to claim 1, wherein the at least one processor is configured to adjust the relative angle according to a drive position of the biopsy device.

8. The control device according to claim 1, wherein the at least one processor is configured to adjust a projection position of a projection image by the projector according to a drive position of the biopsy device.

9. The control device according to claim 1, wherein the at least one processor is configured to adjust the relative angle according to a position of a compression plate provided on the imaging surface side of the imaging table.

10. The control device according to claim 1, wherein the at least one processor is configured to correct a distortion of a projection image that is caused by the projector and occurs in a case where the relative angle is set to the tilt angle.

11. The control device according to claim 1, wherein the at least one processor is configured to control the arm such that the relative angle is a preset tilt angle regardless of an imaging condition in a case where biopsy using a longitudinal puncture is performed by the biopsy device.

12. The control device according to claim 1, wherein the at least one processor is configured to control the arm such that the relative angle is a predetermined angle in a case where the biopsy device interferes with a projection region by the projector, the predetermined angle being an angle at which a light shielding region by the biopsy device that is included in a projection image by the projector has an area equal to or smaller than a predetermined area.

13. A system comprising:

the control device according to claim 1; and a mammography apparatus.

14. A non-transitory storage medium storing a program causing a computer to perform control processing of a mammography apparatus, the mammography apparatus including a biopsy device, an imaging table, and an arm in which a radiation irradiator and a projector are provided on one end portion side and a relative angle between the radiation irradiator and an imaging surface of the imaging table is changeable, the radiation irradiator emitting radiation for imaging of a radiation image toward the imaging surface of the imaging table, the control processing comprising:

controlling the arm such that the relative angle is a predetermined tilt angle in a case where biopsy using a longitudinal puncture is performed by the biopsy device.

15. The non-transitory storage medium according to claim 14, wherein the control processing comprising:

controlling the arm such that the relative angle is a predetermined angle in a case where the biopsy device interferes with a projection region by the projector, the predetermined angle being an angle at which a light shielding region by the biopsy device that is included in a projection image by the projector has an area equal to or smaller than a predetermined area.

* * * * *